United States Patent [19]

Mayer

[11] Patent Number: 5,285,775
[45] Date of Patent: Feb. 15, 1994

[54] SURGICAL BREATHING BAG HAVING HOUR-GLASS SHAPE AND NON-SLIP SURFACE

[76] Inventor: Michael J. Mayer, 1419 Gregory, Apt. 13, Ypsilanti, Mich. 48197

[21] Appl. No.: 878,503

[22] Filed: May 5, 1992

[51] Int. Cl.⁵ .................. A62B 7/00; A61M 16/00; A61M 16/10; A61M 15/00
[52] U.S. Cl. .................. 128/205.13; 128/204.18; 128/203.12
[58] Field of Search ............ 128/203.28, 204.28, 128/205.13, 205.14, 205.15, 205.16, 205.17, DIG. 24, 728, 730, 767, 204.18, 203.12; 417/234, 437, 454, 455, 470–475, 480, 572, 531; 604/310, 319, 322, 342, 408, 410

[56] References Cited

U.S. PATENT DOCUMENTS

| | | | |
|---|---|---|---|
| 297,427 | 4/1884 | MacGregor | 128/203.28 |
| 2,677,371 | 5/1954 | Serra . | |
| 3,009,459 | 11/1961 | Ruben | 128/205.13 |
| 3,262,446 | 7/1966 | Stoner | 128/205.13 |
| 3,356,100 | 12/1967 | Seeler | 128/205.13 |
| 3,859,997 | 1/1975 | Douma et al. | 128/205.17 |
| 4,239,038 | 12/1980 | Holmes . | |
| 4,254,882 | 3/1981 | Yoshino . | |
| 4,294,366 | 10/1981 | Chang . | |
| 4,305,389 | 12/1981 | Potter | 128/205.13 |
| 4,374,521 | 2/1983 | Nelson et al. | 128/205.13 |
| 5,076,452 | 12/1991 | Hashimoto . | |
| 5,080,244 | 1/1992 | Yoshino . | |
| 5,233,977 | 8/1993 | Blankenship et al. | 128/205.13 |

Primary Examiner—Edgar S. Burr
Assistant Examiner—Kimberly L. Asher
Attorney, Agent, or Firm—Richard C. Litman

[57] ABSTRACT

A manually-operated surgical breathing bag for artificial respiration of human beings. The subject bag includes a gas tight, elastomeric, self-expanding and preferably elongated hollow body and an attached port which serves as both a gas inlet and outlet opening. The bag's elongated hollow body is provided with an "hourglass" configuration having a narrowed central portion as an aid for grasping. In order to apply artificial respiration to an individual, the hollow body is grasped with one hand, the fingers spanning the periphery of the hollow body at its narrowed central portion, and compressed with this hand thereby expelling gas toward an individual's lungs.

12 Claims, 3 Drawing Sheets

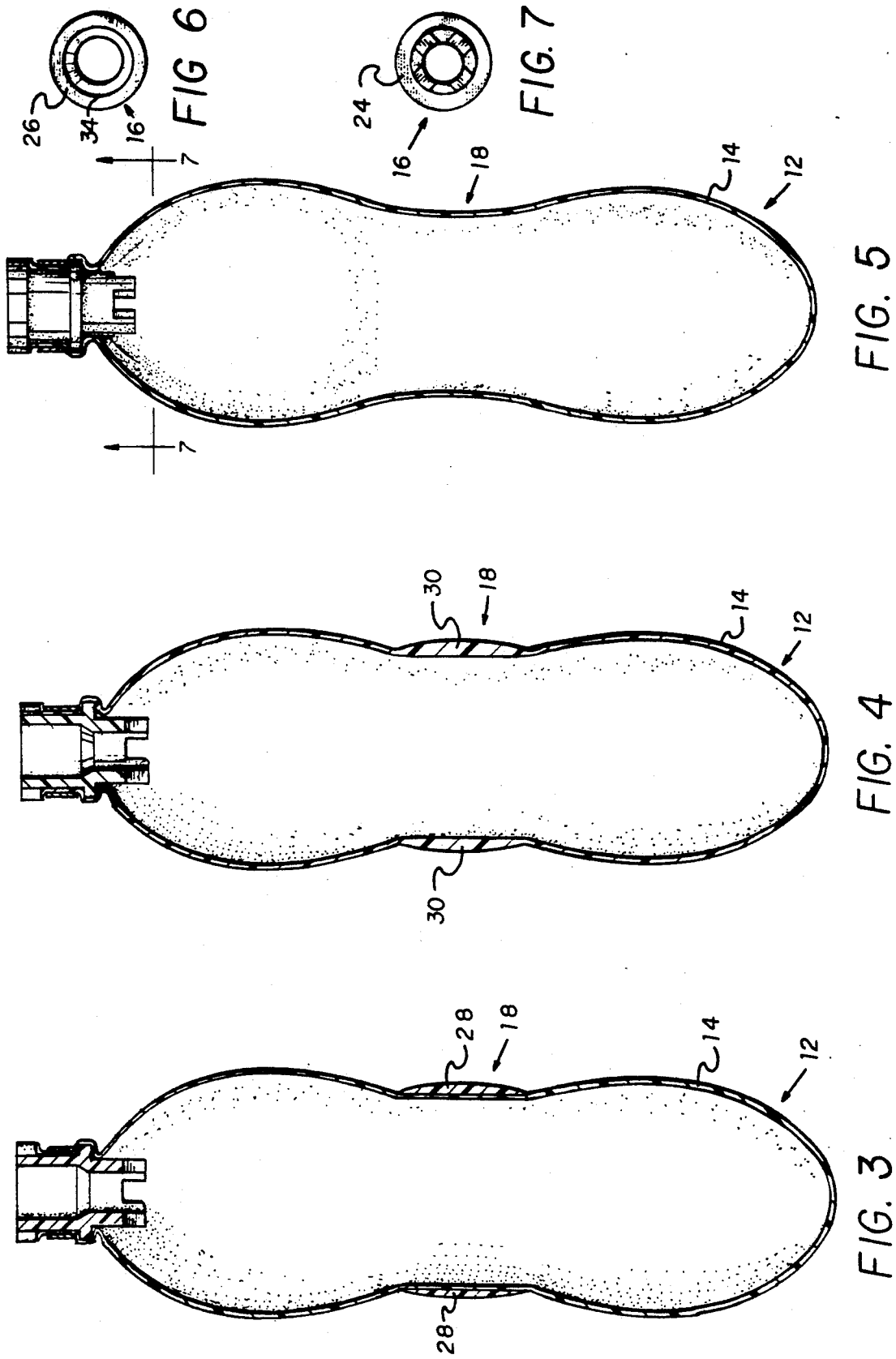

SURGICAL BREATHING BAG HAVING HOUR-GLASS SHAPE AND NON-SLIP SURFACE

FIELD OF THE INVENTION

The present invention relates generally to respiratory devices for use during medical procedures. In particular, a manually operated pump element capable of supplying respiratory gas under pressure which may be easily grasped when wet is disclosed.

BACKGROUND OF THE INVENTION

During surgical procedures, patients unable to breathe for themselves generally require the assistance of skilled medical technicians or doctors to prevent their suffocation. To force oxygen into the lungs of such a patient, a manually operated pump element connected to a remote oxygen supply is often utilized. The pump, usually in the form of an inflatable and resilient breathing bag, is periodically voided to deliver required gases to the patient. Unfortunately, the conventional breathing bag requires manual manipulation or squeezing to drive gas therefrom. During surgery, however, the protective gloves worn by medical personnel often becomes covered with fluids, such as blood, which make the grasping of the bag difficult. Unorthodox methods have been utilized to manipulate breathing bags under extreme circumstances wherein a handgrip could not be established. Such a state of affairs is obviously unsatisfactory in the life or death setting surrounding a surgical procedure. A need exists, therefore, for a surgical breathing bag capable of delivering an adequate supply of oxygen and anesthetic gases to an unconscious patient and which may be grasped by medical personnel under any conditions. It is believed that a device having an "hourglass" configuration will meet this need.

DESCRIPTION OF THE RELATED ART

Manually operated pump elements with an hourglass configuration have been developed to resolve a variety of medical issues. None, however, are seen to address the slippery problem of being difficult, if not impossible, to grasp and manipulate when wet. For instance, U.S. Pat. No. 2,677,371, issued May 4, 1954 to M. A. Loredo Serra, shows a breathing bag having two lobes connected by a narrow passage comprising part of a closed anesthesia administering system. Three ports located within the bag permit gas entry and exit therefrom for circulating anesthetic gas throughout the system. Nevertheless, this bag may not be easily grasped or squeezed at its center due to its narrow width and the presence of a centrally positioned port. Additionally, U.S. Pat. No. 4,239,038, issued Dec. 16, 1980 to Ronald W. Holmes, discloses a twin-lobed resuscitator having a gas reservoir and reservoir bladder connected together by a rigid valve. The valve permits a reserve of breathable gas stored in the bladder to replenish the reservoir under certain conditions. This valve prevents the bag from being squeezed at its narrowed center. Finally, U.S. Pat. No. 4,374,521, issued Feb. 22, 1983 to Thomas W. Nelson et al, describes a cylindrical resuscitator bag which may be squeezed into an hourglass configuration to drive gas therefrom. The hourglass configuration of the particular bag is not retained after such squeezing, however.

Flexible bottles presenting an hourglass appearance have been developed by other industries. In particular, the beverage industry employs such bottles as a means for storing product and delivering such to consumers. U.S. Pat. Nos. 4,254,882, 4,294,366, 5,076,452, and 5,080,244 disclose such bottles. Unfortunately, the rigidity of the materials utilized in their manufacture precludes their use in a surgical breathing apparatus.

None of the above inventions and patents, taken either singly or in combination, is seen to describe the instant surgical breathing bag as claimed.

SUMMARY OF THE INVENTION

The improved surgical breathing bag provided by this invention involves, in addition to the more detailed constructional and operational advances hereinafter described and which can be fully explained and appreciated only in the context of such more detailed consideration, the construction of such a bag in an "hourglass" configuration which may be readily grasped, compressed, and manipulated when wet.

It is an object of the invention to provide improved elements and arrangements thereof in a surgical breathing bag for the purposes described which is inexpensive, dependable and fully effective in accomplishing its intended purposes.

These and other objects of the present inventive surgical breathing bag will become readily apparent upon further review of the following specification and drawings.

BRIEF DESCRIPTION OF THE DRAWINGS

FIG. 3 is a sectional view of the surgical breathing bag of FIG. 1.

FIG. 4 is a sectional view of a surgical breathing bag according to a second embodiment of this invention.

FIG. 5 is a sectional view of a surgical breathing bag according to a third embodiment of this invention.

FIG. 6 is a top view of the nozzle.

FIG. 7 is a bottom view of the nozzle.

Similar reference characters denote corresponding features consistently throughout the attached drawings.

DETAILED DESCRIPTION OF THE PREFERRED EMBODIMENTS

Figure 1:
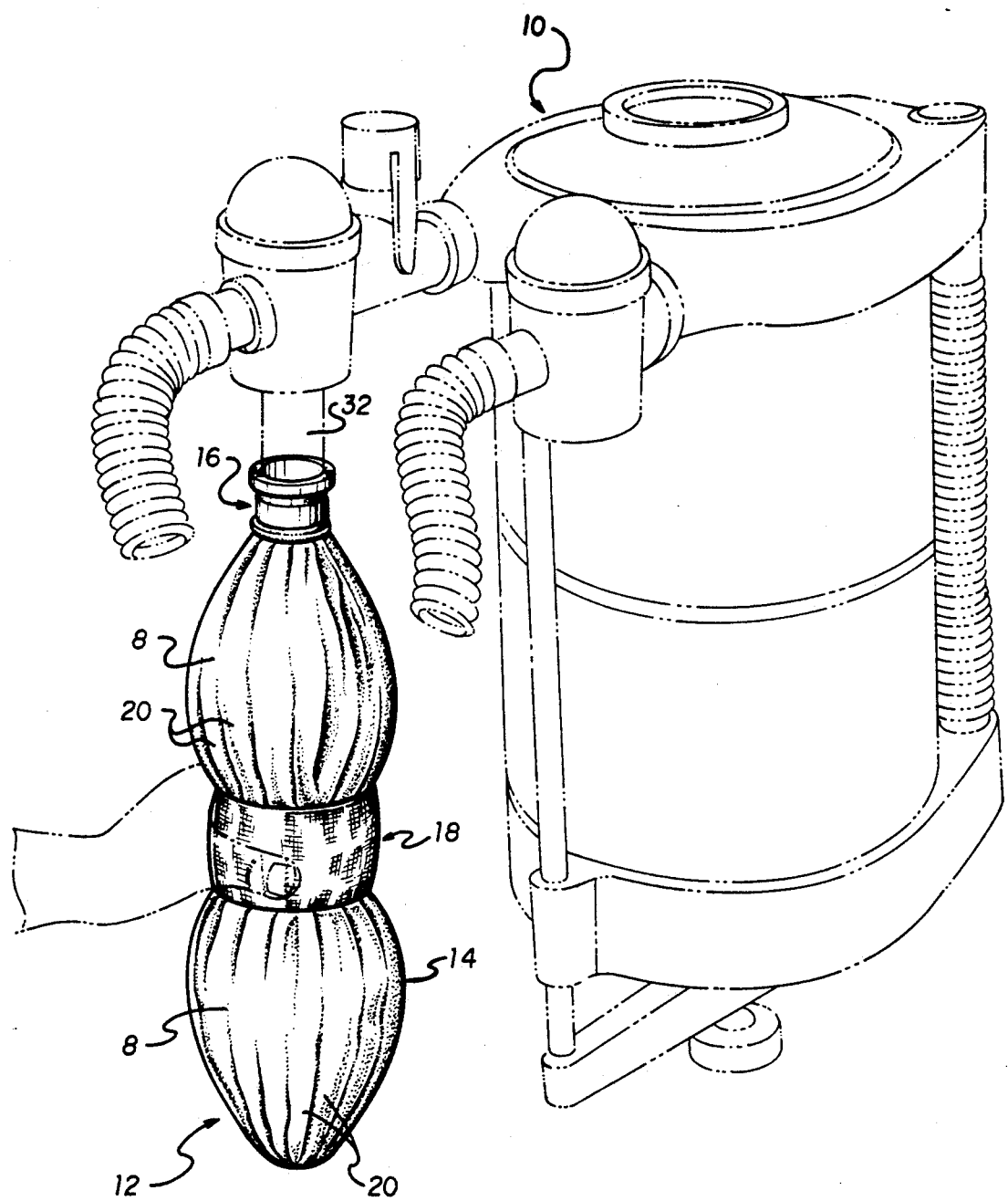
FIG. 1 is an environmental perspective view of a surgical breathing bag according to one embodiment of this invention mounted upon an anesthesia machine shown in broken lines.

Referring now to the embodiments of the invention shown in the drawings by way of example only, FIG. 1 shows an anesthesia machine 10 to which surgical breathing bag 12 is secured. Bag 12 includes a gas tight, elastomeric, self-expanding and preferably elongated hollow body or bladder 14 and an attached nozzle 16 serving as both a gas passageway and a means of attachment to machine 10. Bladder 14 is provided with an "hourglass" configuration reflected in a narrowed central portion or "waist" 18, capable of being easily grasped and manipulated by the hand. Enlarged lobes 8 comprising portions of bladder 14 located to either side of waist 18 are somewhat larger in diameter than waist 18 and provide gas storage reservoirs. The surface of bladder 14 is provided with a series of vertically arranged pleats or folds 20 positioned around its circumference forming alternating recessed or projecting corrugations. In its collapsed position, pleats 20 permit bag 12 to be stored in a container or pouch, for example, of minimal volume. It is envisioned, however, that other bladder embodiments may be constructed without pleats and having a smooth walled surface. Neither surface arrangement of bladder 14 will impact upon the ability of bag 12 to be grasped in the hand about waist 18.

Bladder 14 may be constructed in a range of volumetric capacities and from a variety of materials, selection of which for a particular application being dictated by physiological and medical requirements. Bladders having a capacity of one liter are generally suitable for small infants. A two liter capacity is suitable for adolescents and adults of small stature, while a bladder having three liter capacity would be utilized in medical situations involving most adults. Nevertheless, bladders having capacities other than those expressed here may be constructed with equal facility. Materials suitable for bladder construction include: rubber, flexible plastics, and various elastomers.

Figure 2:
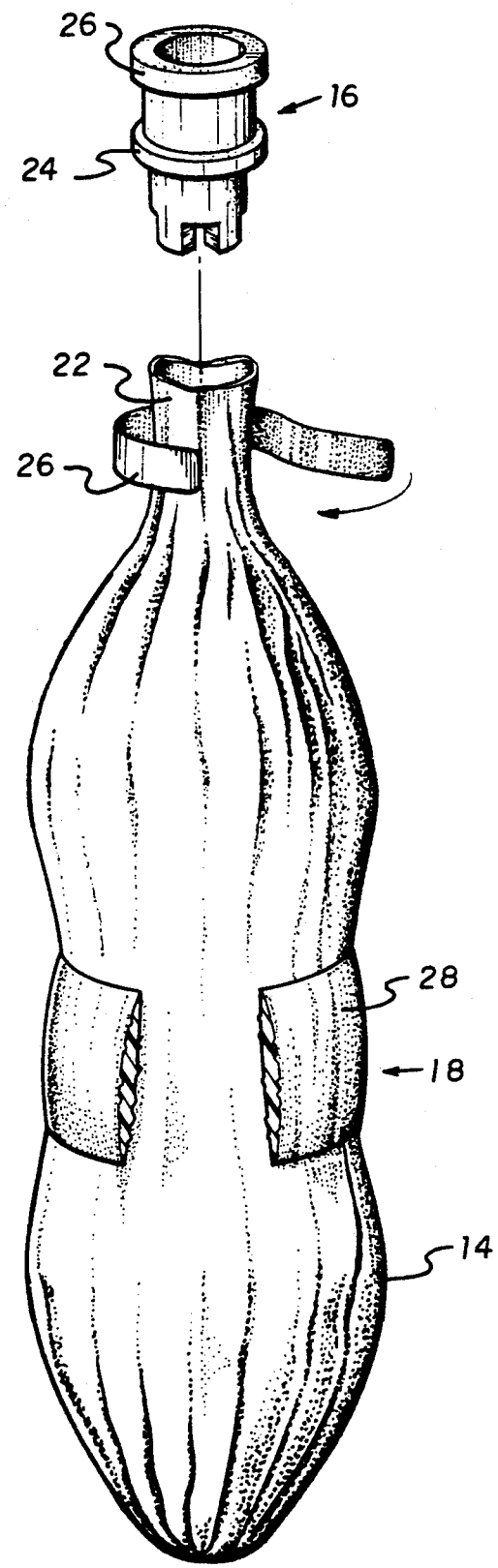
FIG. 2 is an exploded perspective view of the surgical breathing bag of FIG. 1 with parts broken away.

Referring to FIG. 2, the means of attachment of nozzle 16 to bladder 14 is shown. To join the aforesaid components, throat portion 22 of elastomeric bladder 14, having a relaxed diameter smaller in diameter than that of nozzle 16, is initially stretched and expanded such that its diameter is increased beyond that of lock ring 24 of nozzle 16. Nozzle 16 is then inserted into throat 22. After insertion, lip 26 remains upon the exterior of bladder 14. Throat 22 is next permitted to relax from its stretched condition onto nozzle 16. Finally, adhesive and substantially inelastic tape 26 is circumferentially wrapped about throat 22 above lock ring 24 securely joining nozzle 16 and bladder 14 together.

Surgical breathing bag 12 can be provided with an hourglass configuration in several ways. Three such examples are illustrated herein, but should not be considered as exclusive of other means of accomplishing the same result. Referring now to FIGS. 2 and 3, bag 12 is seen fitted with a circular band 28 of flexible material. As band 28 has a smaller diameter than the surrounding bladder material, inflation of bladder 14 with respiratory gas produces narrow waist 18 capable of being easily grasped. In order to apply artificial respiration to an individual, waist 18 is grasped with one hand, the fingers spanning its periphery, and compressed with this hand thereby expelling gas toward an individual's lungs. In this, the principal embodiment of the instant invention, band 28 is produced from an inelastic material experiencing minimal deformation or stretching when bag 12 pressurized. Thus, the diameter of waist 18 remains relatively constant regardless respiratory gas pressure exerted upon the interior walls of bag 12. Nonetheless, it is envisioned that band 28, of a material with somewhat more elastic qualities, may provide a suitable substitute for its inelastic counterpart. For this reason, band 28 may be constructed from a variety of materials, including among others: rubber, plastic, various polymers, and natural plant fibers such as cotton. Into these materials may be woven or molded: a textured surface pattern, surface irregularities, or other features to assist in producing a non-slip surface which may be readily grasped by the hand. When utilizing ring 28, bladder 14 may be produced in a variety of configurations to accommodate such. In the principal embodiment of instant invention, bladder 14 is molded or otherwise produced with an hourglass shape and a narrowed waist substantially similar in diameter to that of ring 28. The narrow waist provided to bladder 14 assists in the attachment of ring 28 to bladder 14 by providing a seating surface therefor. It remains possible however to manufacture bladder 14 without a narrowed waist but rather having a substantially cylindrical shape of constant diameter along its length. In either configuration, ring 28 may be joined to bladder 14 by any manner or method known in the art. By way of example, permanent bonds may be obtained by adhesives or the application heat to melt opposing materials together. Temporary attachment may be accomplished by sliding the two components together for a friction fit of ring 28 and bladder 14. Referring now to FIG. 4, a second embodiment of the invention is shown. In this particular embodiment, bladder 14 is provided with a thickened wall 30 at waist 18. Wall 30 provides the functional features of ring 28 of the principal embodiment but is integrally formed with bladder 14. Waist 18 of this second embodiment may also be provided with a textured surface, not shown, enhancing its ability to be gripped. FIG. 5 illustrates a third embodiment of the invention. In the third embodiment, bladder 14, having walls of constant thickness, is provided with an hourglass configuration. Neither a ring 28, as was disclosed in the principal embodiment of FIGS. 2 and 3, or a thickened wall 30, as was shown in the second embodiment of FIG. 4, are present at waist 18. A textured surface, not shown, may be provided to waist 18 as well as the entire bag to enhance the ability of bag 12 to be gripped and manipulated. This third embodiment of the invention is the least expensive of the three embodiments to manufacture since material and assembly requirements are minimized.

FIGS. 6 and 7 show nozzle 16 from above and below. Nozzle 16, illustrated as part of the instant invention, is both well known in the art and compatible with most anesthesia machines currently in use. It is shown for illustrative purposes, however, and other nozzle configurations may be employed in the instant invention with equal effectiveness. This said, nozzle 16, comprised of a resilient material such as rubber or soft plastic, may be stretched to fit upon regulator pipe 32 of anesthesia machine 10 shown in FIG. 1. Interior wall 34 of nozzle 16 has a circumference slightly smaller than that of pipe 32 permitting secure frictional attachment of bag 12 to machine 10. Under normal operating conditions, this seal will not leak anesthetic gas into the operating room environment where the instant surgical breathing bag will be utilized.

It is to be understood that the present inventive breathing bag is not limited to the several embodiments described above, but encompasses any and all embodiments within the scope of the following claims.

I claim:

1. A manually operable surgical breathing bag for the artificial respiration of human beings, comprising:
a gastight, elastomeric hollow body, essentially circular in cross section having a generally elongated hourglass shape defining a narrowed waist portion, two enlarged lobes having an exterior diameter greater than that of said narrowed waist portion and joined thereby, a throat portion open at its upper end and adapted to receive a nozzle therein, and a circular band of flexible material having a textured, non-slip surface and a width substantially similar to that of said narrow waist portion, said circular band being positioned between said enlarged lobes.

2. The surgical breathing bag according to claim 1 further comprising:

a nozzle joined to said hollow body as a gas inlet and outlet opening.

3. The surgical breathing bag according to claim 1, wherein said hollow body is self-expanding.

4. The surgical breathing bag according to claim 1, wherein said hollow body is comprised of rubber.

5. The surgical breathing bag according to claim 1, wherein said hollow body further includes:

pleats positioned around the circumference of said body forming alternating recessed and projecting corrugations.

6. The surgical breathing bag according to claim 1, wherein said narrowed waist portion includes:

a textured, non-slip surface.

7. The surgical breathing bag according to claim 1, wherein said nozzle includes:

a circular lip at the top of said nozzle; and
a circular lock ring positioned below said lip.

8. The surgical breathing bag according to claim 7, further including:

adhesive tape circumferentially wrapped about said throat portion and between said lip and said lock ring, whereby said nozzle is joined to said hollow body by said tape.

9. The surgical breathing bag according to claim 1, wherein said band is comprised of one of the following: rubber, plastic, and natural plant fiber.

10. The surgical breathing bag according to claim 1, wherein said hollow body further comprises:

a wall of constant thickness.

11. The surgical breathing bag according to claim 1, wherein said hollow body further comprises:

a wall, said wall being variable in thickness and being of greater thickness at said waist portion than throughout the remainder of said hollow body.

12. A manually operable surgical breathing bag for the artificial respiration of a human being, comprising:

a gastight, elastomeric hollow body, essentially circular in cross section, having a generally elongated hourglass shape, means for manual operation by a user comprising a narrowed waist portion having a textured, non-slip surface, two enlarged lobes having an exterior diameter greater than that of said narrowed waist portion and joined thereby, and a throat portion open at its upper end and adapted to receive a nozzle therein;

a circular band of flexible material positioned between said lobes and having a width substantially similar to that of said waist, said band being comprised of one of the following:

rubber, plastic, and natural plant fiber;

a nozzle positioned within said throat portion as a gas inlet and outlet opening said nozzle connected to a source of respiratory gas, and including:

a circular lip at the top of said nozzle, and
a circular lock ring positioned below said lip; and adhesive tape circumferentially wrapped about said throat portion and between said lip and said lock ring, said nozzle joined to said hollow body by said tape.

* * * * *